United States Patent [19]
Cook

[11] Patent Number: 5,354,260
[45] Date of Patent: Oct. 11, 1994

[54] SLIPPER WITH AN INFLATABLE FOOT PUMP

[75] Inventor: Gordon J. Cook, Andover, United Kingdom

[73] Assignee: Novamedix, Ltd., Walworth, United Kingdom

[21] Appl. No.: 62,437

[22] Filed: May 13, 1993

[51] Int. Cl.5 ............................................. A61F 5/00
[52] U.S. Cl. ..................... 602/13; 602/27; 602/65; 128/DIG. 20; 601/22; 601/149
[58] Field of Search ............... 128/24 R, 64, DIG. 20, 128/53, 60, 61; 602/13, 27, 65; 36/29, 148, 153

[56] References Cited

U.S. PATENT DOCUMENTS

| Re. 32,939 | 6/1989 | Gardner et al. | |
| 1,304,915 | 5/1919 | Spinney | 36/153 |
| 2,708,930 | 5/1955 | Lowman | 602/27 |
| 4,721,101 | 1/1988 | Gardner et al. | 128/64 |
| 4,832,010 | 5/1989 | Lerman | 602/65 |
| 5,139,479 | 8/1992 | Peters | 602/65 |
| 5,176,624 | 1/1993 | Kuehnreich | 602/65 |

FOREIGN PATENT DOCUMENTS 0635094 3/1934 Fed. Rep. of Germany ........ 602/27

Primary Examiner—Richard J. Apley
Assistant Examiner—Jeanne M. Mollo
Attorney, Agent, or Firm—Hopgood, Calimafde, Kalil & Judlowe

[57] ABSTRACT

A one-piece slipper construction, into which an inflatable foot-pump bag or bladder is permanently integrated and wherein a thin reinforcement panel is fully contained and located within a flat-foldable wrap, for selective completion of the circumferential tie that is needed for assurance of stimulated foot-pump action. In the preferred embodiment, the wrap is so further devised as to provide a flexibly reinforced, non-stretch backing reference for a laterally extending portion of the inflatable bag, for active stimulation of the adjacent dorsi-medial region, where further blood accumulates as part of the pool from which venous return flow can be driven.

13 Claims, 3 Drawing Sheets

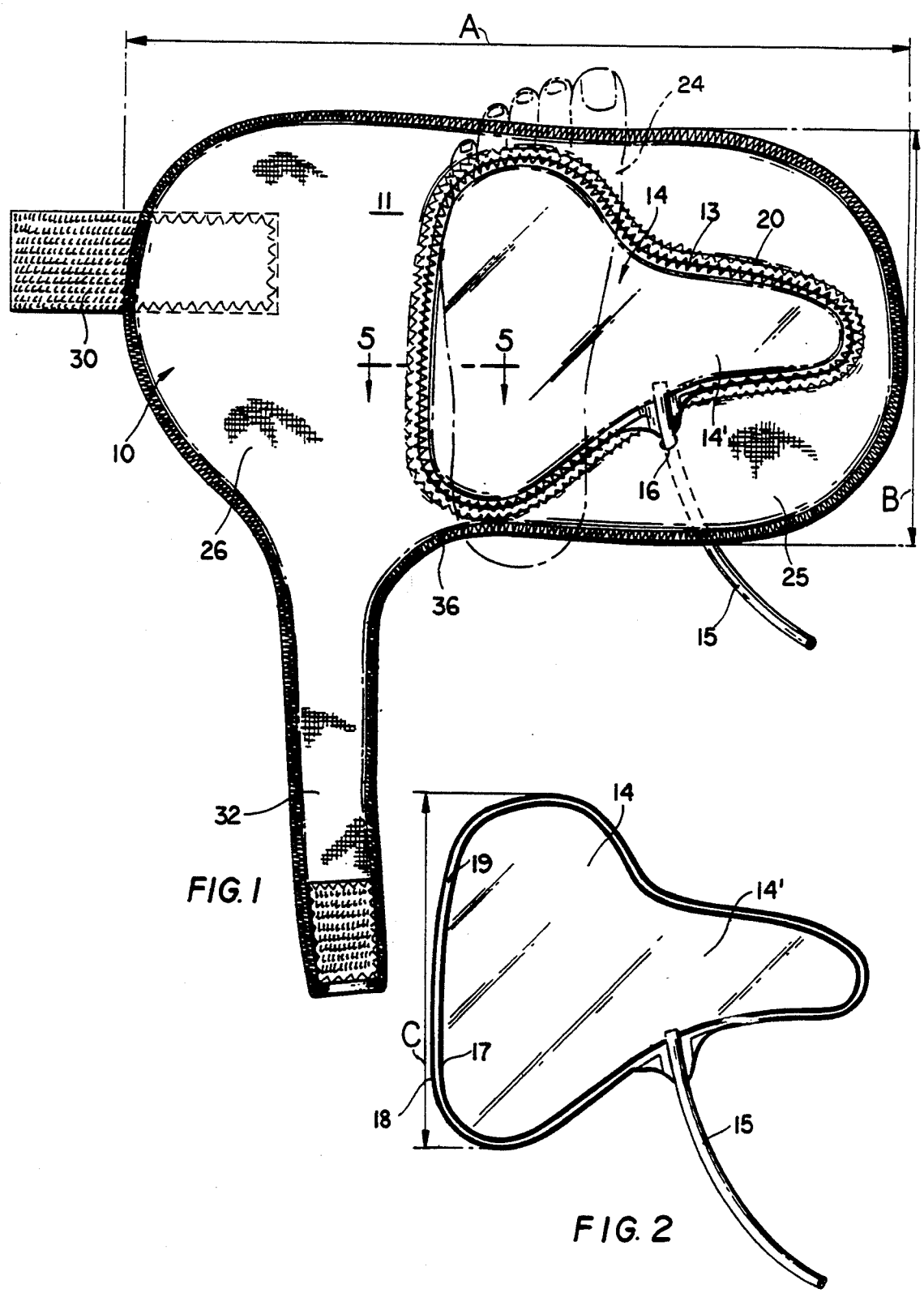

SLIPPER WITH AN INFLATABLE FOOT PUMP

BACKGROUND OF THE INVENTION

The invention relates to a medical device known as a foot pump for therapeutic application of transient squeezing action on the pool of blood which accumulates in the plantar region of a foot and which is normally returned for recycled use, via the venous system serving the human leg. The invention represents an improvement with respect to devices disclosed in U.S. Pat. No. Re. 32,939, and the disclosures of said reissue patent are incorporated herein by reference.

The devices of said reissue patent had their origin in the inventors' discovery that in a normal ambulatory human being, the very fact of walking, wherein body weight is alternated in application first to one leg and then to the other, has the normal effect, in response to weight-bearing, of transiently forcing apart the ball and heel of the foot, followed by a relaxation process in which the load of body weight is transferred to the other foot. As a result, the vessels in which blood accumulates in the plantar region between the ball and heel are transiently stretched to reduce blood-vessel section area, and blood is expelled for return to the heart via the venous system. For bed-ridden patients and those having a limited range of ambulation, the normal processes of venous return necessarily suffer, and the impulse-driven inflatable foot pump is proving ever more helpful, even if primarily only to reduce pain in a leg injury.

The said reissue patent discloses a fitted slipper, for use with an applied inflatable bag, and the patent also suggests incorporating an inflatable bag in a boot, to enable a patient's limited ambulation, while temporarily disconnected from the source of pulsed inflation air required for foot-pump operation. But the fitted slipper and the suggested boot are devoid of any suggestion of how to provide maximum comfort, convenience of application and removal, all at such low cost as to classify the item as disposable, i.e., not reusable by another patient.

BRIEF STATEMENT OF THE INVENTION

It is the object of the invention to provide an improved slipper construction, incorporating its own inflatable foot-pump structure, and featuring (1) ease of application to and removal from a patient, (2) materially enhanced comfort in use, and (3) such low cost, light weight, and flat foldability as to be regarded as expendable, i.e., recommended for single-patient use.

The invention achieves this object in a one-piece construction into which an inflatable foot-pump bag or bladder is permanently integrated and wherein a thin reinforcement panel is fully contained and located within a flat-foldable wrap, for selective completion of the circumferential tie that is needed for assurance of stimulated foot-pump action. In the preferred embodiment, the wrap is so further devised as to provide a flexibly reinforced, non-stretch backing reference for a laterally extending portion of the inflatable bag, for active stimulation of the adjacent dorsi-medial region, where further blood accumulates as part of the pool from which venous return flow can be driven.

DETAILED DESCRIPTION

The invention will be described for its presently preferred embodiment, in conjunction with the accompanying drawings, in which:

FIG. 1 is a plan view of the exposed upper surface of a foldable slipper or wrap of the invention, laid flat and open, in readiness for wrapped application to a left foot which is shown by phantom outline to have been properly positioned;

FIG. 2 is a plan view of the inflatable-bladder component of the foldable slipper of FIG. 1;

The complete article of FIG. 1 is seen to comprise an assembly of component subassemblies, secured to a flexible base member or wrap 10, which in shoe-construction parlance should perhaps be called an "upper" but which, due to the need to differentiate between its upper surface 11 and its lower surface 12, will not be referred to as the "upper".

Figure 3:
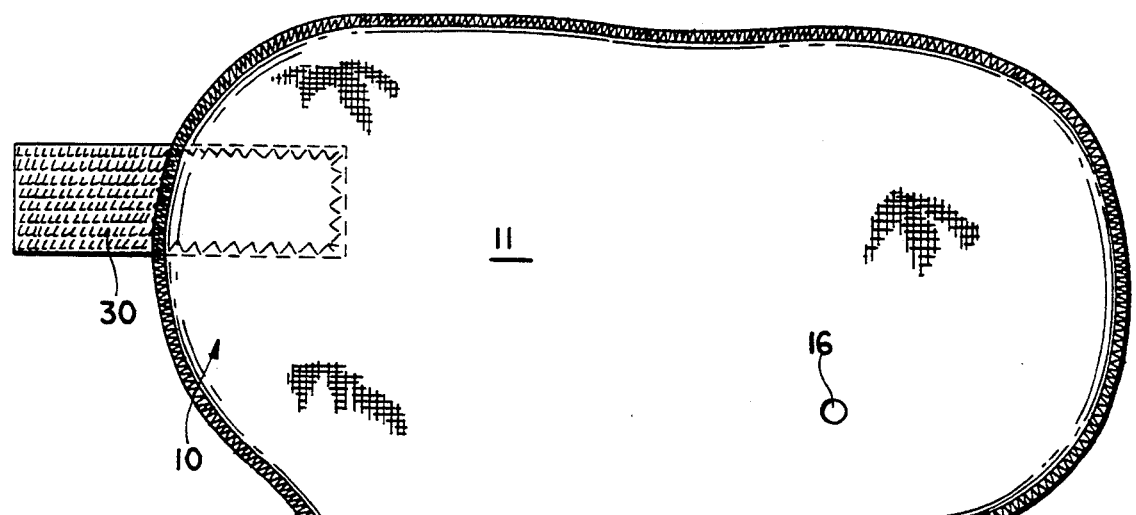
FIG. 3 is a plan view of the wrapping component of the foldable slipper of FIG. 1.

Secured by a peripheral succession of stitches 13 to the upper surface 11 of wrap 10 is an inflatable bladder 14, which is suitably an edge-seam-welded consolidation of two like panels of flexible plastic sheeting having the shape most clearly shown in FIG. 2. A flexible inflation tube 15 has sealed access through the upper panel of bladder 14 and, when assembled to wrap 10, the inflation tube extends through an aperture 16, which is seen in FIG. 3 to have been a feature of wrap 10 prior to assembly of bladder 14 thereto. As seen in FIG. 2, the seamed peripheral edge of bladder 14 preferably features spaced inner and outer bead formations 17, 18 which are shown by continuous heavy lines. The space 19 between these bead formations is characterized by a flat double-thickness weld of the two bladder panels, for ease of stitching-needle entry, and so that, for the case of zig-zag stitching, lateral zig-zag excursions of the stitching 13 can straddle the outer-bead formation 18, for enhanced retention of bladder 14 to wrap 10; the inner-bead formation will be seen to enhance the edge-sealed integrity of the inflatable envelope of bladder 14, against egress of inflation air.

Figure 4:
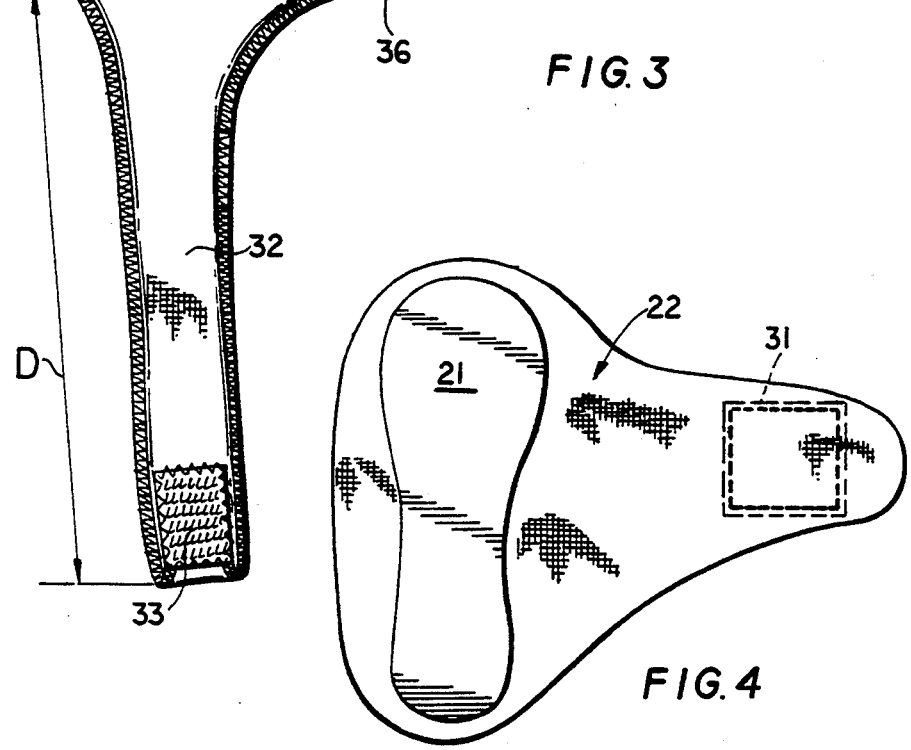
FIG. 4 is a plan view of reinforcement structure which is a component of the foldable slipper of FIG. 1.

FIG. 4 depicts a reinforcement or stiffener subassembly which is secured to the lower surface of wrap 10, by a peripheral succession of zig-zag stitches 20 which are seen in FIG. 1 to be adjacent to and laterally external of the stitches 13. This subassembly comprises a thin stiff panel 21, as of plywood, cut to correct size for the intended use, and serving as the "shank" of the slipper of FIG. 1. The shank panel 21 need only be adhered, as by double-stick tape (not shown) to a "canvas" panel 22 having a plan configuration which conforms to but peripherally continuously exceeds the plan configuration of bladder 14. The body of canvas panel 22 is preferably of two-ply construction, tightly woven to exhibit virtually no stretch in any direction. The shank panel 21 is adhered to the upper surface of this two-ply construction, and for quiet engagement with floor surfaces, the two-ply construction is finished with a bottom-laminated panel 23 (see FIG. 5) of knitted-loop nylon.

Returning again to FIGS. 1 and 3, wrap 10 is seen to have an initially flat body of elongate, generally oval or rectangular form, with a length dimension A which is substantially double its width dimension B. As can be noted from the phantom outline 24 of a foot at its intended placement on the bladder 14 in FIG. 1, the width dimension B is selected for the particular foot size, such that the length of the foot is centrally astride wrap 10 and projects beyond both limits of the width dimension B, so that the toes and the heel of the foot will be exposed. The shank panel 21 will be understood to be in register with and beneath that portion of bladder 14 which has the maximum extent C in the length direction of the foot, thereby assuring a stiff reinforcing reaction to bladder inflation in the plantar region of the foot and between the ball and heel of the foot.

In addition to the bladder area devoted to action upon the indicated plantar region of the foot, bladder 14 is seen to be further characterized by an inflatable region 14' which extends laterally inward of the foot and which, when wrapped around the foot, will provide bladder-inflation therapy to the dorsi-medial region.

Figure 6:
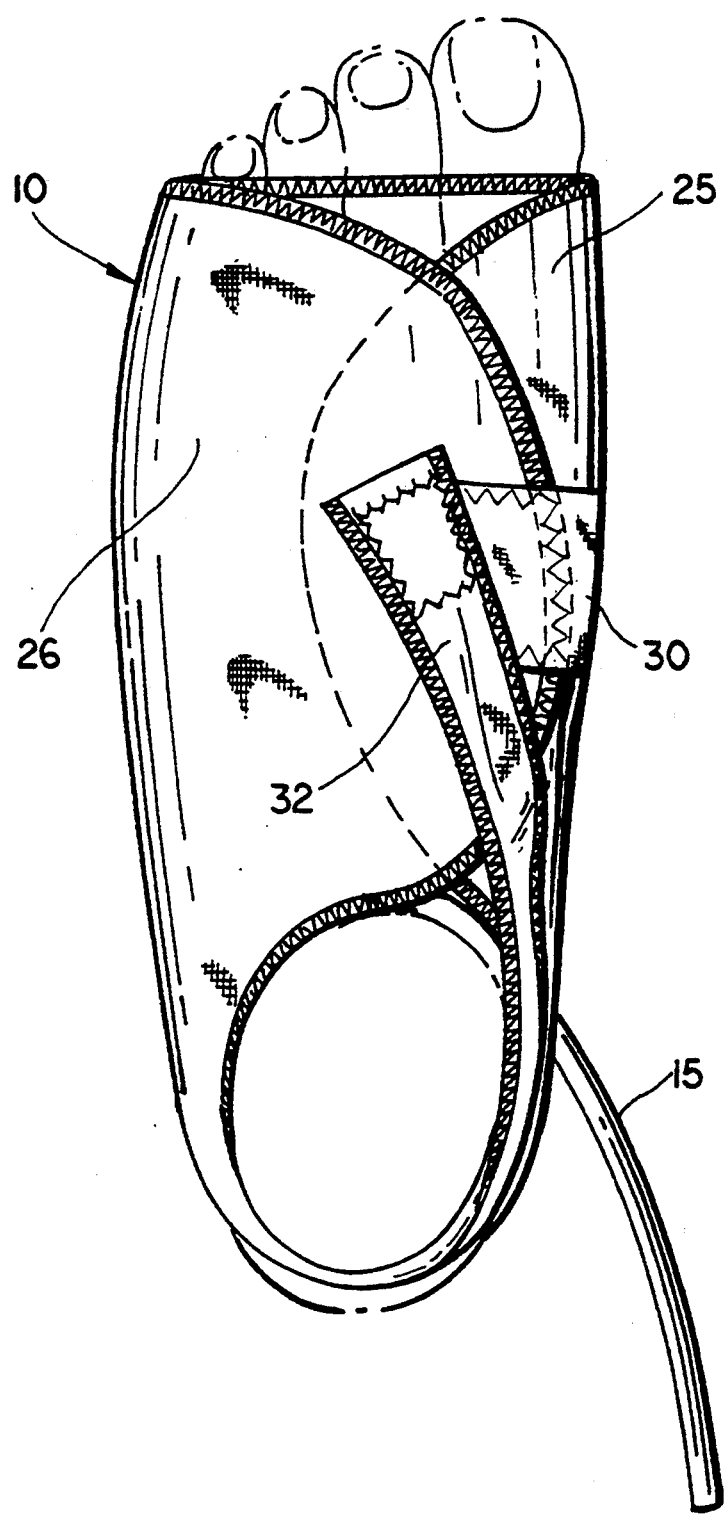
FIG. 6 is a plan view, slightly enlarged from the scale of FIGS. 1 to 4, to show a completely wrapped application of the slipper of FIG. 1 to the left foot of a patient, as seen from substantially the elevation of the patient's ankle.

To have provided for foot placement centrally astride the width dimension B of wrap 10 is to leave laterally inward and laterally outwardly extending major areas 25, 26 of wrap 10 available for wrapped assembly to each other, over the dorsum of the foot, as depicted in FIG. 6. Of these, the laterally inward area 25 is to hold bladder region 14' for direct action on the foot, whereas the laterally outward area 26 is to be in securely retained overlapping engagement with area 25, thus establishing a circumferential tie around the dorsum of the foot. In the form shown, provision is made to releasably hold such a circumferential tie, using "touch-and-close" fastener materials which are suitably "hook-and-loop" materials known under the trade name VELCRO. As shown, a tab patch 30 of one such material (preferably the "hook" variety) is stitched to and outwardly projects from area 26 of wrap 10, and another patch 31 of coacting material is suggested by dashed lines to have been sewn to the underside of the laminated stiffener-panel structure of FIG. 4. As explained below, the patch 31 may be dispensed with if the material of the bottom-laminated panel 23 will removably engage to the hook material of tab patch 30.

As security that wrap 10 will be retained as a circumferential tie of bladder 14 in intended position, the flat configured plan of wrap 10 also integrally features a strap formation 32 which extends to an extent D beyond the wrap 10 area (A × B), in generally parallel relation to the length direction of the foot, but offset laterally outward of the foot alignment. The strap formation 32 is thus an integral formation of the laterally outer area 26 of wrap 10, which is the outer exposed area after wrapping to achieve the circumferential tie. And having achieved the circumferential tie, strap 32 is available for wrap around the back of the heel or ankle, as shown in FIG. 6, for tensed engagement of its patch 33 of hook material to exposed loops of a loosely woven ply 12 of the composite material of wrap 10.

Figure 5:
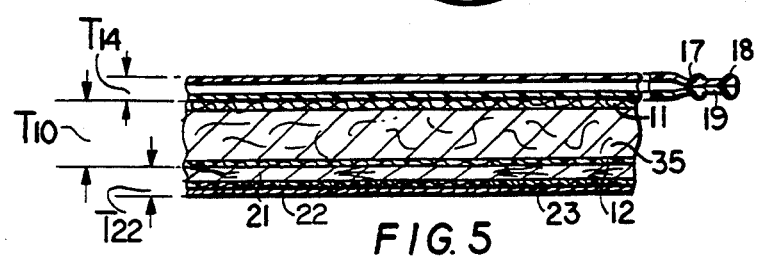
FIG. 5 is an enlarged and exaggerated fragmentary section, taken at 5—5 of FIG. 1.

Attention is now directed to the enlarged and exaggerated fragmentary section of FIG. 5 for identification and discussion of materials. In FIG. 5, the respective thickness labels adopt as subscripts the reference numerals used in discussion above. Thus, the dimension labelled $T_{14}$ indicates overall thickness identifiable with components of bladder 14, namely its upper and lower panels of flexible sheet plastic; also indicated is their edge-welded seam which features the inner and outer bead formations 17, 18 and the flat 19 between these bead formations. The dimension labelled $T_{10}$ similarly indicates thickness of bonded components of wrap 10, and the dimension $T_{22}$ indicates thickness of the stiffener panel, including its tightly woven canvas and its laminated outer-finish 23 layer of knitted-loop nylon.

Within the thickness $T_{10}$, wrap 10 is seen to be a bonded composite, built on a central core 35 which may be a commercially available slab of foamed polyester/polyurethane compound, suitably 5 to 10 mm thick and preferably of standard 8 mm thickness. The upper bonded layer 11 is suitably a scrim, and the lower bonded layer 12, as well as the lower bonded panel 23, are of such loosely woven or knitted-loop construction, as of nylon, that they are detachably securable to the hook material of tab 30, whether or not patch 31 is available.

The description of wrap 10 is completed by identifying the peripheral or outer so-called "overlocking" border stitch 36 which finishes off the entire profile of wrap 10. This stitch will be understood to compress foam material 35 as it ties the registering plies 11 and 12' to each other. Suitably, the material for border stitch 36 is a polyester filamentary core, wound with cotton. The same may be said for the stitching material at 13 and 20, where the gauge of the stitching material may be of lesser weight.

The described construction will be seen to achieve above-stated objects and to be of such design as, for a given slipper size, to serve a relatively wide range of patients' shoe sizes, and the bladder itself is reversible, to serve both right-foot and left-foot embodiments, thus minimizing inventory requirements. The construction features ease of application to and removal from a patient's foot, so that each patient can be served by his own slipper, throughout his period of confinement and/or therapy. The circumferential tie to the patient's foot, in conjunction with the reinforcement panel 21, assures maximum effectiveness of foot-pump stimulation, even though the slipper may have been removed for a period between successive uses.

What is claimed is:

1. A medical appliance, comprising an elongate generally rectangular and flexible wrap having between upper and lower surfaces a length dimension (A) which is approximately twice its width dimension (B), wherein said width dimension is adapted to approximate but extend short of the length dimension of a human foot that is to be subjected to foot-pump therapy for enhancement of venous and arterial flow; a relatively stiff reinforcement panel that is adapted to be sufficiently elongate to lap the span between the ball and heel of the foot, securing means retaining said relatively stiff reinforcement panel in assembly with said wrap at the lower surface of said wrap and at a location that is generally central with respect to said length dimension (A), with the elongate direction of said reinforcement panel transverse to said length dimension (A); an inflatable bladder comprising two peripherally sealed panels of impervious flexible plastic material, said bladder being secured to the upper surface of said wrap at least in substantial register with said reinforcement panel and said bladder being adaptively shaped for active force application to the plantar region substantially only between the ball and heel of the foot; said securing means including a flexible reinforcing panel of tightly woven essentially non-stretch fabric adhered to said relatively stiff panel and having a perimeter which overlaps said relatively stiff panel and which has at least lapping conformance to the periphery of said bladder, said flexible reinforcement panel having peripherally stitched retention to said wrap in substantial conformance with the periphery of said bladder; said wrap having laterally extending remainder portions with means for removably securing the same in lapped circumferentially tied relation to each other over the dorsi-medial region of a foot that has been placed in register with said bladder and said reinforcement panel; and an elongate heel strap connected to said wrap, said strap extending from one to the exclusion of the other of said remainder portions and from one to the exclusion of the other of the elongate sides of said wrap and generally parallel to but laterally offset from alignment with said reinforcement panel; whereby when said wrap has been circumferentially tied around the foot, said strap may be secured around the back of the heel to the other of the lateral remainder portions of said wrap.

2. The medical appliance of claim 1, which said strap is an integral formation of said wrap.

3. The medical appliance of claim 1, in which said wrap comprises first and second laminated plies of woven fabric respectively defining said upper and lower surfaces.

4. The medical appliance of claim 3, in which said wrap further comprises a ply of compliant foamed material between said first and second plies.

5. The medical appliance of claim 4, in which said plies are peripherally continuously stitched together.

6. The medical appliance of claim 3, in which the seal of said flexible plastic panels defines a peripherally continuous bladder-sealing rim of substantially constant width, said bladder being secured to said wrap by a peripheral succession of stitching which is limited to stitched piercing of plastic bladder material solely within said rim.

7. The medical appliance of claim 1, in which the sealed panels of said bladder are not only configured to lap the longitudinal plantar region between the ball and heel of the foot but are further configured to define an integrally formed dorsi-medial area which extends transversely from the lapped plantar region of the bladder, the dorsi-medial area of the said bladder being within and fully lapped by one of the lateral remainder portions of said wrap.

8. The medical appliance of claim 6, in which said flexible reinforcement panel additionally has peripherally stitched retention to said bladder-sealing rim.

9. The medical appliance of claim 8, in which said bladder has an externally accessible and sealed flexible-tube connection through one of the plastic bladder panels near an edge portion of the dorsi-medial area of the bladder, and in which external access of said tube is via a tube-locating aperture in said wrap.

10. The medical appliance of claim 4, in which the sealed panels of said bladder are not only configured to lap the plantar region between the ball and heel of the foot but are further configured to define an integrally formed dorsi-medial area which extends transversely from the lapped plantar region of the bladder, the dorsi-medial area of the bladder being within and fully lapped by one of the lateral remainder portions of said wrap, the seal of said bladder panels defining a peripherally continuous sealing rim of substantially constant width enclosing both the plantar and dorsi-medial areas of the bladder, said bladder being secured to said wrap by a peripheral succession of stitching which is limited to stitched piercing of plastic-bladder material solely within said rim.

11. The medical appliance of claim 10, wherein said flexible reinforcement panel provides a peripherally continuous rim of panel reinforcement outwardly of the periphery of said bladder and said peripheral stitching is limited to said rim of panel reinforcement.

12. The medical appliance of claim 11, in which the rim of said bladder comprises spaced inner and outer bead formations, said stitching lapping the outer to the exclusion of the inner one of said bead formations.

13. The medical appliance of claim 1, in which touch-and-close fastening means are carried at outer longitudinal limits of said wrap and of said strap, for selective retention of an installed application of said appliance to a foot.

* * * * *